US008772506B2

(12) United States Patent
Inoue et al.

(10) Patent No.: US 8,772,506 B2
(45) Date of Patent: Jul. 8, 2014

(54) 1,3-DIIODOHYDANTOIN COMPOUND AND PRODUCTION METHOD THEREOF

(75) Inventors: Kazuhisa Inoue, Isumi (JP); Yukihiko Hanamura, Isumi (JP); Takaaki Miyazawa, Chuo-ku (JP)

(73) Assignee: Nippoh Chemicals Co., Ltd., Tokyo (JP)

( * ) Notice: Subject to any disclaimer, the term of this patent is extended or adjusted under 35 U.S.C. 154(b) by 570 days.

(21) Appl. No.: 12/926,900

(22) Filed: Dec. 16, 2010

(65) Prior Publication Data

US 2011/0092714 A1    Apr. 21, 2011

Related U.S. Application Data

(63) Continuation of application No. 11/991,285, filed as application No. PCT/JP2006/317113 on Aug. 30, 2006, now Pat. No. 7,897,785.

(30) Foreign Application Priority Data

Sep. 2, 2005 (JP) ................................. 2005-255557

(51) Int. Cl.
*C07D 233/82* (2006.01)
(52) U.S. Cl.
CPC .................................. *C07D 233/82* (2013.01)
USPC ...................................................... 548/320.5
(58) Field of Classification Search
CPC ................................................... C07D 233/82
USPC ....................................................... 548/320.5
See application file for complete search history.

(56) References Cited

U.S. PATENT DOCUMENTS

| | | | | |
|---|---|---|---|---|
| 2,795,556 | A * | 6/1957 | Quinn | 252/187.33 |
| 4,012,565 | A | 3/1977 | Freedman et al. | |
| 4,100,348 | A | 7/1978 | Habermeier et al. | |
| 5,780,641 | A * | 7/1998 | Yerushalmi et al. | 548/320.5 |
| 5,953,456 | A | 9/1999 | Ikeda et al. | |

FOREIGN PATENT DOCUMENTS

| | | |
|---|---|---|
| EP | 0 785 192 A1 | 7/1997 |
| JP | 9-316057 A | 12/1997 |
| JP | 2002-030072 A | 1/2002 |
| JP | 2002-275008 | 9/2002 |
| WO | WO 02/08227 A2 | 1/2002 |

OTHER PUBLICATIONS

Orazi et al. (J. Org. Chem., 1965, vol. 30, p. 1101-1104).*
Stahl et al. (Int. J. Pharm. (Feb. 21, 2002), 233(1-2); pp. 227-237).*
http://hyperphysics.phy-astr.gsu.edu/hbase/kinetic/vappre.html—Vapor Pressure—Oct. 1999.*
Extended European Search Report issued Sep. 28, 2012 in EP 12180060, European Patent Office, Munich, DE, 5 pages.
Extended European Search Report issued Oct. 2, 2012 in EP 12180061, European Patent Office, Munich, DE, 5 pages.
Official Action issued in U.S. Appl. No. 12/926,899, Sep. 14, 2012, United States Patent and Trademark Office, USA, 14 pages.
Kouniaki, Sofia, et al., The effect of high hydrostatic pressure on anthocyanins and ascorbic acid in blackcurrants (*Ribes nigrum*), Flavour and Fragrance Journal, 2004, vol. 19, pp. 281-286, John Wiley & Sons, Ltd., NJ, US (published online Mar. 29, 2004 in Wiley InterScience (www.interscience.wiley.com). DOI: 10.1002/ffj.1344.
Office Action ("Communication pursuant to Article 94(3) EPC") issued Feb. 3, 2012, in corresponding European Patent Application No. 06 797 085.5, 5 pages, European Patent Office, Munich, DE.
Office Action issued Feb. 24, 2011, in corresponding Chinese application No. 200680031821.5 and English translation thereof.
Orazi et al., "N-Iodohydantoins. II.[1,2] Iodinations with 1,3-Diiodo-5,5-Dimethylhydantoin" *Journal of Organic Chemistry*, Apr. 1965, pp. 1101-1104, vol. 30.
Raab et al., "Carbon-14 Labeling of a Trifluoromethoxy Group: Synthesis of a Substance P Antagonist" *Journal of Labelled Compounds and Radiopharmaceuticals*, 2001, pp. 815-829, vol. 44, John Wiley & Sons, Ltd.
English-language version of the International Preliminary Report on Patentability and Attached Written Opinion (Forms PCT/IB/326, PCT/IB/373 and PCT/ISA/237) mailed by the International Bureau on Mar. 13, 2008 in corresponding PCT/JP2006/317113, The International Bureau of WIPO, Geneva, Switzerland.
International Preliminary Report on Patentability and Attached Written Opinion (Forms PCT/IB/338, PCT/IB/373 and PCT/ISA/237) mailed by the International Bureau on Sep. 25, 2008 in corresponding PCT/JP2006/317113, The International Bureau of WIPO, Geneva, Switzerland.
Office Action issued Feb. 5, 2010 in corresponding Chinese Application No. 2006800318215 and English language translation thereof.
Supplementary European Search Report issued Jun. 18, 2010 in corresponding EP Application No. 06797085.5.
J. H. Harker et al., "Drying", *Chemical Engineering*, Jan. 1, 2002, pp. 901-969, vol. 2, Chapter 16. Elsevier Butterworth-Heinemann.
Japanese Industrial Standard Handbook 49, Version 2004, Chemical Analysis, front page English language translation only.
English language T 0990/96-3.3.1.

(Continued)

*Primary Examiner* — Yong Chu
*Assistant Examiner* — Valerie Rodriguez-Garcia
(74) *Attorney, Agent, or Firm* — Buchanan Ingersoll & Rooney P.C.

(57) ABSTRACT

The present invention provides a means which can inhibit release of $I_2$ in production or storage of 1,3-diiodohydantoin compound, and thereby solve decrease in purity of the compound and various problems caused by $I_2$. The present invention provides a production method for 1,3-diiodohydantoin compound comprising a step to prepare a wet body containing a 1,3-diiodohydantoin compound, and (1) a step to dry the wet body by contacting the wet body with heated gas or (2) a step to lyophilize the wet body, a storage method for 1,3-diiodohydantoin compound comprising a step to store a 1,3-diiodohydantoin compound under a temperature condition of 15° C. or lower, and a 1,3-diiodohydantoin compound wherein content of released $I^2$ is 1% by mass or less.

4 Claims, No Drawings

(56) References Cited

OTHER PUBLICATIONS

A Notification issued Jul. 9, 2010, in corresponding Japanese Patent Application No. 2007-533295, and English translation thereof.
Presentation of Publications and the Like and English translation thereof.
Felix Franks, "Freeze-drying of bioproducts: putting principles into practice," *European Journal of Bioharmaceuticals*, 1998 (month unknown), pp. 221-229, vol. 45, Elsevier Science B.V.
PCT/ISA/210, PCT/ISA/220, and PCT/ISA/237.
Office Action issued on May 9, 2013, in corresponding Indian Patent Application No. 858/KOLNP/2008.

* cited by examiner

US 8,772,506 B2

1,3-DIIODOHYDANTOIN COMPOUND AND PRODUCTION METHOD THEREOF

CROSS REFERENCE TO RELATED APPLICATIONS

This application is a continuation of application Ser. No. 11/991,285, filed Feb. 29, 2008, which was the National Stage filing under §371 of PCT/JP2006/0317113, filed Aug. 30, 2006, which claims priority to Japanese Patent Application No. 2005-255557, filed Sep. 2, 2005, the entire content of each of which is incorporated herein by reference.

TECHNICAL FIELD

The present invention relates to 1,3-diiodohydantoin compound and production method thereof. More in detail, the present invention relates to improvement in long-term stability of the aforementioned compounds.

BACKGROUND ART 1,3-Diiodohydantoin compound (hereinafter, also simply referred to as "DIH compound") has been widely used as a sensitive material for photography or the like, or an iodizing agent or an oxidizing agent in production processes for medical drugs, agricultural chemicals, chemicals, or the like.

As a method for producing the DIH compounds, for example, a technique, in which a hydantoin compound is reacted with iodine monochloride in the presence of a base in an aqueous solution, has been disclosed (see, for example, JP-A-2002-30072 and J. Org. Chem., 30 (1965), 1101-1104). Such technique has advantageous points that it is simple and highly efficient as well as easy post-treatments such as purification and waste liquid treatment.

Here, in the specification of JP-A-2002-30072, a technique for purifying a DIH compound from reaction system has been described as "deposited crystal is collected by filtration, and the resultant crystal is dried under a reduced pressure".

Meanwhile, the DIH compounds produced by the techniques or the like described in the above literatures are usually stored until the time to be used for the above applications. As such a storage method, for example, a technique, in which the compound is stored under a reduced pressure and nitrogen atmosphere in a dark place, has been disclosed (see, for example, J. Labelled Compd. Radiopharm., 44-12 (2001), 815-830).

DISCLOSURE OF THE INVENTION

However, there is no description about the DIH compounds superior in easy handling and good storage stability, it has been revealed from the study by the present inventors that there is a problem that the aforementioned DIH compound tends to decrease in purity when the DIH compound is produced by the production method described in the above literature or when the DIH compound is stored by a common method as described in the above literature. Such decrease in purity is considered to be caused by release of iodine atom as an elementary substance ($I_2$) of iodine by decomposition of the iodine compound. The release of $I_2$ could cause problems such as coloration or corrosion of material or equipment by aforementioned $I_2$ and increased risk for operators.

Thus, an object of the present invention is to provide a means to inhibit release of $I_2$ in production or storage of DIH compound, and thereby solve decrease in purity of DIH compound or various problems caused by $I_2$.

In order to solve the above problems, the present inventors intensively searched for a cause of release of $I_2$ in production or storage of DIH compound.

As a result, the present inventors have found that DIH compound is unstable in a state of wet body, in which a certain level of liquid component such as water and an organic solvent is contained, even at an ordinary temperature, and that this instability causes the aforementioned release of $I_2$. In addition, the release of $I_2$ from such wet body becomes more remarkable under a comparatively high temperature condition.

Therefore, based on the above knowledge, the present inventors have found that the decomposition of DIH compound and the release of $I^2$ accompanying thereto can be prevented by controlling drying means in production of DIH compound and temperature condition in storage thereof, and finally accomplished the present invention.

That is, the present invention provides a production method for 1,3-diiodohydantoin compound comprising a step to provide a wet body containing a 1,3-diiodohydantoin compound, and (1) a step to dry the wet body by contacting the wet body with heated gas or (2) a step to lyophilize the wet body.

In addition, the present invention provides a storage method for a 1,3-diiodohydantoin compound comprising a step to store a 1,3-diiodohydantoin compound under a temperature condition of 15° C. or lower.

Further, the present invention provides a 1,3-diiodohydantoin compound wherein content of released $I_2$ is 1% by mass or less.

According to the present invention, release of $I_2$ during production or storage of DIH compound can be inhibited, and thereby decrease in purity of DIH compound or incidence of various problems caused by $I_2$ can be prevented.

BEST MODE FOR CARRYING OUT THE INVENTION

A first aspect of the present invention relates to a production method for DIH compound. Specifically, firstly a wet body containing a DIH compound is provided. Subsequently, (1) the wet body is dried by contacting the wet body with a heated gas, or (2) the wet body is lyophilized.

As described above, it has been found out that DIH compound is unstable in a state of wet body, in which a certain level of liquid component is contained therein, and the instability causes the release of $I_2$ as described above. In addition, it has been also found out that such release of $I_2$ becomes remarkable under a comparatively higher temperature condition. In the present invention, a method to inhibit effectively this release of $I_2$ is provided.

Incidentally, although mechanism of the release of $I_2$ in production or storage of DIH compound has not been necessarily clarified, a mechanism based on decomposition of the DIH compound has been presumed. However, such mechanism is only a presumption, and even if the release of $I_2$ occurs via another mechanism, the technical scope of the present invention is not affected at all.

Hereinafter, the production method of the first aspect of the present invention will be explained in detail.

Firstly, the first step in the production method of the first aspect of the present invention, that is, the step in which a wet body containing a DIH compound is provided will be described.

In the present invention, "DIH compound" means a compound represented by the following chemical formula (I):

[Formula 1]

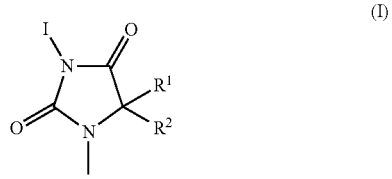

(wherein $R^1$ and $R^2$ are each independently a hydrogen atom or a $C_1$-$C_6$ alkyl group).

Way of procurement for the wet body containing a DIH compound is not particularly limited. The wet body containing a DIH compound may be used by synthesizing according to the well known technique (e.g. the technique described in the aforementioned JP-A-2002-30072) or may be used by purchasing a commercially available product. As a technique to prepare the wet body containing a DIH compound by oneself, for example, the technique shown below can be used. However, the following preparation method is only an example, and it is needless to say that "wet body containing a DIH compound" prepared by a technique other than the following mode may be used.

In the present invention, the DIH compound (Chemical Formula (I)) is prepared, for example, by reacting a hydantoin compound (Chemical Formula (II)) with iodine monochloride in the presence of a base in an aqueous solution, as shown in the following Chemical Reaction Scheme 1.

[Formula 2]

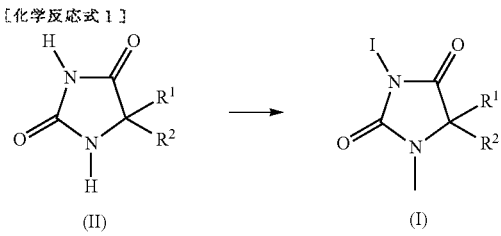

wherein $R^1$ and $R^2$ are as defined above.

In order to prepare the DIH compound according to the Chemical Reaction Scheme 1, firstly a hydantoin compound represented by the Chemical Formula (II), which is used as a raw material, is provided.

[Formula 3]

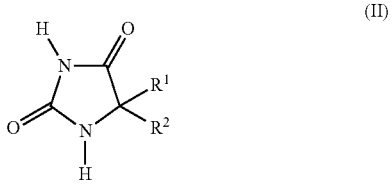

wherein $R^1$ and $R^2$ are as defined above.

As described above, $R^1$ and $R^2$ is each a hydrogen atom or a $C_1$-$C_6$ alkyl group. $R^1$ and $R^2$ may be same or different from each other. In view of yield in the synthesis reaction and easiness in handling, $R^1$ and $R^2$ are preferably identical to each other. The alkyl group may be linear, branched or cyclic. Number of carbon atoms in the alkyl group is 1 to 6, preferably 1 to 2, and more preferably one. Specific example of the alkyl group includes methyl group, ethyl group, propyl group, isopropyl group, butyl group, isobutyl group, s-butyl group, t-butyl group, pentyl group, isopentyl group, neopentyl group, hexyl group, and the like. An alkyl group other than these may also be used. Among them, preferably both of $R^1$ and $R^2$ are methyl groups, from the viewpoints of industrially moderate price and easy availability.

Way of procurement for the hydantoin compound (II) is not particularly limited. The hydantoin compound may be used by synthesizing according to the well known technique or may be used by purchasing a commercially available hydantoin compound.

Iodine monochloride is a compound represented by the chemical formula of "ICl", and highly reactive due to containing iodine of (oxidation number+1), and used in various synthetic reactions as an iodizing agent.

Way of procurement for iodine monochloride (ICl) is also not particularly limited. Iodine monochloride may be used by synthesizing according to the well known technique or may be used by purchasing commercially available iodine monochloride. Incidentally, as a technique to synthesize iodine monochloride by oneself, for example, a technique is exemplified, in which chlorine is passed over iodine, then liquefied and distilled. It is needless to say that iodine monochloride synthesized by other technique may also be used.

The reaction of a hydantoin compound and iodine monochloride is carried out in the presence of a base. This base acts as a catalyst in the reaction system containing a hydantoin compound and iodine monochloride.

Specific mode of the base is not particularly limited, and a base which commonly used in such synthetic reaction can be similarly used. An example of the base includes, for example, hydroxides, carbonate salts and the like of alkali metals/alkaline earth metals such as sodium hydroxide, potassium hydroxide, sodium carbonate, sodium hydrogen carbonate, potassium carbonate, potassium hydrogen carbonate, and the like. It should be noted that these bases may be used alone or in combination of two or more kinds.

The above reaction is carried out in an aqueous solution, but a solvent other than water may be included therein. For example, amide type solvents and ester type solvents can be included.

Compounding ratio of each component in the above reaction is not particularly limited, and conventionally known knowledge (in particular, aforementioned JP-A-2002-30072) can be referred to as appropriate.

After completion of the above reaction, components other than DIH compound are removed from the reaction system. By this operation, a solution of DIH compound can be obtained. Subsequently, most of the solvent contained in the solution is removed. By this operation, a "wet body containing a DIH compound" can be prepared. However, the step in which solvent is removed, may be carried out before removing the components other than the DIH compound.

The technique to remove the components other than DIH compound is not particularly limited, and, for example, a technique such as filtration, recrystallization and extraction, and combination thereof can be exemplified. Other technique may also be used.

In addition, the technique to remove most of the solvent from the solution containing DIH compound is also not particularly limited, and, for example, a technique such as filtration, centrifugal separation and decantation, and combination thereof can be exemplified. Other technique may also be used.

In this regard, the "wet body containing a DIH compound" to be provided in this step is composed of a DIH compound, a solvent, and in some case a small amount of impurity, but content of the solvent in the wet body is not particularly limited. As an example, content of solvent is around 8 to 30% by mass to total amount of the wet body. More solvent may be contained in the wet body, but too high content of the solvent could result in prolonged drying time leading to rise of production cost.

Hereinafter, characteristic steps in the production method of the present invention will be explained.

As described above, in the production method of the present invention, regarding the resultant "wet body containing a DIH compound", (1) the wet body is dried by contacting the wet body with a heated gas, or (2) the wet body is lyophilized.

Firstly, the technique (1) is explained in detail.

In the technique (1), the "wet body containing a DIH compound" prepared in the above is dried by contacting the wet body with a heated gas. Namely, in the technique (1), so called "fluidized drying" is employed.

Conventionally, as a technique to dry the wet body containing a DIH compound, an industrially common drying method had been employed. Specifically, drying method by heating under reduced pressure, e.g. using a conical dryer, drying method by heating under ordinary pressure, e.g. using a plate column dryer, and the like had been employed. However, the present inventors have found out that a part of the wet body containing a DIH compound decomposes and $I_2$ is released by these methods. Specifically, when a wet body of a DIH compound (5,5-dimethyl body) containing 2 to 15% of water is heated at 40° C. for 3 hours, 4 to 6% of the compound is decomposed to release $I_2$. Also, when the wet body is similarly heated at 70° C. for 3 hours, 9 to 30% of the compound is decomposed. As a result, such problems as decrease in purity of DIH compound, and coloration or corrosion of material or equipment by released $I_2$, and increased risk for operators could occur.

On the contrary, according to the technique as described above, the release of $I_2$, which had conventionally been a problem in drying a wet body, can be inhibited to the minimum. In this regard, although mechanism, by which a difference in levels of released $I_2$ arises between the conventional drying technique and the drying technique of the present invention, has not been perfectly clarified, it is considered that the DIH compound which is instable to heat may decompose because the wet body is exposed at a high temperature condition over a long period of time in such unit of several hours in the conventional drying technique. Consequently, according to the production method of the present invention, not only the release of $I_2$ in production of DIH compound can be inhibited to the minimum, but also heating time can be reduced and rapid production is enabled, and this can contribute to reduction in production cost. However, the technical scope of the present invention should be determined based on the description in the claims, and the technical scope is not affected by the mechanism.

Specific mode of the fluidized drying is not particularly limited, and conventionally well known knowledge in the synthesis field of chemical compounds can be referred to as appropriate. Hereinafter, preferable mode in the fluidized drying is exemplified. However, fluidized drying is not limited only to the following mode.

In the present invention, "heated gas" means a gas having a temperature level at which a wet body containing a DIH compound can be dried by contacting with the wet body. The heated gas is preferably a gas which does not react with the DIH compound. Specific kind of the heated gas includes, for example, nitrogen gas, argon gas, helium gas, air gas, and mixed gas thereof, but kind of the heated gas is not limited to them. As the heated gas, air gas is preferably used.

Temperature of the heated gas in contact with aforementioned wet body is not particularly limited, and can be decided taking physical properties of the DIH compound to be prepared and general knowledge in fluidized drying into consideration comprehensively. However, temperature of the heated gas is preferably 20 to 200° C., more preferably 40 to 170° C., and furthers more preferably 90 to 130° C. Too low temperature of the heated gas requires prolonged drying time as a result of insufficient amount of heat, or could fail to dry up to a desired liquid content. On the contrary, too high temperature of the heated gas could give rise to deterioration (decomposition and melting) of the DIH compound due to overheating.

Flow rate of the heated gas in contact with aforementioned wet body is also not particularly limited, but preferably 0.1 to 10.0 m/sec, more preferably 0.3 to 5.0 m/sec, and further more preferably 0.5 to 3.0 m/sec. Too low flow rate of the heated gas requires prolonged drying time as a result of insufficient contact of the heated gas with the whole wet body, or could fail to dry up to a desired liquid content. On the contrary, too high flow rate of the heated gas could make collection of the wet body difficult because of excessive scattering of the wet body.

Next, the technique (2) is explained in detail.

In the technique (2), the "wet body containing a DIH compound" provided as described above is lyophilized. By such technique, the release of $I_2$, which had conventionally been a problem in drying of the wet body, can also be inhibited to the minimum. In this regard, mechanism by which the conventional problem is solved by employing lyophilization is presumed to be similar to the case of the aforementioned fluidized drying.

Thus, the techniques (1) and (2) are the same in the point to inhibit the release of $I_2$ in drying the wet body to the minimum.

"Lyophilization" is also referred to as lyophilize, and a technique in which a wet body is dried by freezing quickly the wet body at a temperature of the freezing point or below, and removing a solvent of the frozen body by sublimation by reducing pressure to a level of the vapor pressure of the solvent or below.

Specific mode of the lyophilization is not particularly limited, and conventionally well known knowledge in the synthesis field of chemical compounds can be referred to as appropriate. Hereinafter, a preferable mode in the lyophilization is exemplified. However, the lyophilization is not limited to the following mode.

Firstly, a wet body containing a DIH compound is cooled down quickly to a prescribed temperature. By this operation, the aforementioned wet body is frozen. Temperature to be attained by the quick cooling is not particularly limited, but the wet body may be cooled down to preferably −196 to 0° C., and more preferably −100 to −20° C.

After that, the frozen body is placed in a reduced pressure. In this case, pressure condition is not particularly limited, and pressure may be reduced to a level which is necessary to remove a solvent contained in the wet body. As an example, pressure may be reduced to around 10 to 1,500 Pa, and preferably 100 to 700 Pa.

When the wet body is dried by the technique (2), preferably a solvent is further added to the "wet body containing a DIH compound" provided as described above to prepare a wet body in a slurry state, then the resultant wet body in a slurry state is lyophilized by the technique described above. According to this mode, such desirable effect that sublimation from inside is facilitated by freezing of whole wet body in a slurry state compared with the case when the wet body provided as described above is simply lyophilized as it is, can be obtained.

In such mode, the solvent to be added to the wet body when the wet body in a slurry state is prepared is not particularly limited. However, a solvent, which does not react with the DIH compound and is easy to sublime in the following lyophilization, is preferably used. An example of the solvent to be added includes, besides water, ethyl acetate, n-butyl acetate, N,N-dimethylformamide, and the like. Among them, preferably water is further added from the viewpoints of moderate price, easy-handling, and being suitable for lyophilization.

Addition amount of the solvent when the solvent is added to the wet body is also not particularly limited, but the solvent may be added so that total content of the solvent to the whole amount of the wet body in a slurry state becomes preferably 30 to 70% by mass, and more preferably 50 to 60% by mass.

According to the production method of the first aspect of the present invention, by any technique of (1) and (2), the release of $I_2$ in production of DIH compound can be inhibited to the minimum, and conventional various problems associated with the release of $I_2$ can be solved. In other words, according to the production method of the first aspect of the present invention, a DIH compound which has a more reduced content of released $I_2$ than before can be produced. Namely, a second aspect of the present invention is a DIH compound which has a reduced content of free $I_2$. In this case, content of the free $I_2$ in the DIH compound of the second aspect of the present invention is preferably 1% by mass or less, more preferably 0.8% by mass or less, further more preferably 0.4% by mass or less, and particularly preferably 0.2% by mass or less. As described above, since the free $I_2$ is an impurity to cause various problems, lower content of the free $I_2$ in the resultant DIH compound is more preferable. However, the technical scope of the production method of the first aspect of the present invention is not necessarily limited only to a mode in which a DIH compound containing such amount of the free $I_2$ is produced. In some case, a DIH compound containing the free $I_2$ in an amount out of this range may be produced. In addition, the technical scope of the DIH compound of the present invention is not necessarily limited only to the mode in which the DIH compound is produced by the production method of the first aspect of the present invention, and in some case, the DIH compound may be produced by other production method. In this regard, as a content of free $I_2$ in the DIH compound produced, a value measured by the technique described in Example below should be employed.

In addition, in the DIH compound of the second aspect of the present invention, besides the content of free $I_2$, less content of water is also more preferable. This is because decomposition of DIH compound and release of $I_2$ accompanying thereto in production and storage of DIH compound occur more easily when water content is higher. Specifically, content of water in the DIH compound of the second aspect of the present invention is preferably 6% by mass or less, more preferably 5% by mass or less, further more preferably 3% by mass or less, and particularly preferably 1% by mass. Consequently, when the wet body containing a DIH compound is subjected to fluidized drying (1) or lyophilization (2) in the production method of the first aspect of the present invention, drying conditions may be controlled so that content of water in the resultant DIH compound becomes a value in the above range.

Application of the DIH compound of the second aspect of the present invention is not particularly limited, but it can be employed, for example, in applications such as a sensitive material of photography or an iodizing agent or an oxidizing agent in production processes for medical drugs, agricultural chemicals, chemicals, or the like.

As described above, the production method for DIH compound was explained as the first aspect of the present invention, and the DIH compound itself was also explained as the second aspect of the present invention. The present invention also provides a storage method for DIH compound as a third aspect of the present invention.

The storage method of the third aspect of the present invention has been made based on the knowledge that decomposition of DIH compound and release of $I_2$ accompanying thereto occurs more easily under a comparatively higher temperature condition.

Namely, the third aspect of the present invention is a storage method comprising a step in which a DIH compound is stored under a temperature condition of 15° C. or lower.

The DIH compound to be used in the storage method of the third aspect of the present invention is not particularly limited, and conventionally well known DIH compound can be used. However, in view of sufficient inhibition of decomposition of DIH compound and release of $I_2$ thereby, the DIH compound produced by the production method of the first aspect of the present invention or the DIH compound provided as the second aspect of the present invention is preferably used. Since specific mode of these DIH compounds is as described above, detailed explanation will be omitted here.

In the third aspect of the present invention, the DIH compound is stored under a temperature condition of 15° C. or lower, preferably 10° C. or lower, and more preferably 5° C. or lower. By this operation, the decomposition of DIH compound and the release of $I_2$ thereby can be inhibited.

In the third aspect of the present invention, specific mode other than the storage under the above temperature condition is not particularly limited, and conventionally well known knowledge about storage of chemical compounds can be referred to as appropriate. In this regard, in the present invention, concept of "storage" includes not only a mode when a DIH compound is placed in one position, but also a mode such as "transportation" in which a DIH compound is transferred among various places until it is used for a prescribed application.

In the third aspect of the present invention, humidity condition in the storage of DIH compound is not particularly limited, but generally it is preferable to be stored under a low humidity condition. Specifically, relative humidity (RH) in an atmosphere of storage place is preferably 50% or less, and more preferably 30% or less.

In the storage method of the third aspect of the present invention, DIH compound is usually stored in a packed state in a prescribed container. Specific mode of the container is also not particularly limited, and conventionally well known storage containers in storage field of chemical compounds can be employed as appropriate. Constituent material for the storage containers includes industrially commodity type of resins, and specifically includes polyethylene, polypropylene, polystyrene, polyester, polyvinyl chloride, polyvinylidene chloride, and the like. Shape of the storage containers is also not particularly limited, and shapes such as bag-like, box-like, drum-like, and the like are exemplified.

Even by the storage method of the third aspect of the present invention, a very small amount of $I_2$ can be released from DIH compound during storage. Consequently, the storage container is preferably those having a hermetically sealing function. From such viewpoint, as a constitutional material for the storage containers, polyvinylidene chloride/ polyethylene composite material and high-barrier-performance polymers are preferably employed. Metal containers with resin lining can also be used as the storage containers. However, in such mode, it should be noted that the metal material could be corroded by penetration of a very small amount of free $I_2$ when storage is continued for an extremely long period.

In the storage method of the third aspect of the present invention, the temperature condition is not necessarily in the above range through whole course of storage period, but the temperature condition may be in the above range in about 100% of the period except the period when the DIH compound is temporally stored under a temperature condition of around ordinary temperature because of transfer or the like.

The storage method of the third aspect of the present invention may be combined with the production method of the first aspect of the present invention.

For example, when a DIH compound is premised to be stored using the storage method of the third aspect of the present invention, it is convenient to produce the DIH compound according to the production method of the first aspect of the present invention, then to store directly the DIH compound by the storage method of the third aspect of the present invention.

EXAMPLES

Hereinafter, the present invention will be explained more in detail using Examples and Comparative Example, however, the technical scope of the present invention is not limited to the following modes.

Example 1

As a wet body containing a DIH compound, 5,5-dimethyl-1,3-diiodohydantoin (20 kg) containing n-butyl acetate (2% by mass) and water (13% by mass) was provided.

The wet body provided as described above was charged into a fluidized dryer. The wet body was dried by contacting the wet body with air of 110° C. as a heated gas in a flow rate of 1 msec for 30 minutes to obtain pale yellow crystalline powder of 5,5-dimethyl-1,3-diiodohydantoin in a purity of 98% or more.

After that, contents of free $I_2$ and water in the resultant powder were determined. As a result, content of free $I_2$ was 0.2% by mass or less, and content of water was 1% by mass or less. In this regard, the contents of free $I_2$ and water were measured by the following techniques.

<Measuring Method for Content of Free $I_2$>

According to "First method: Method by heating drying under atmospheric pressure" in JIS-K0067$^{-1992}$ 4.1.4(1) described in "2004-edited JIS Handbook, 49, Chemical Analysis", a sample was heated at 60° C. for 2 hours under the atmospheric pressure, and decrease in mass was measured to obtain a content of free $I_2$.

<Measuring Method for Content of Water>

According to "First method: Method by heating drying under atmospheric pressure" in JIS-K0067$^{-1992}$ 4.1.4(1) described in "2004-edited JIS Handbook, 49, Chemical Analysis", the sample, which was used for measuring content of free $I_2$, was dried at 105° C. for 2 hours under the atmospheric pressure, and decrease in mass was measured to obtain a content of water.

Example 2

As a wet body containing a DIH compound, 5,5-dimethyl-1,3-diiodohydantoin (50 g) containing water (8% by mass) was provided.

The wet body provided as described above was charged into a lyophilizer, then cooled down to −80° C. to freeze the wet body. Subsequently, the resultant frozen body was dried by sublimation at 20° C. for 22 hours under reduced pressure condition of 270 Pa to obtain pale yellow crystalline powder of 5,5-dimethyl-1,3-diiodohydantoin in a purity of 95% or more.

After that, contents of free $I_2$ and water in the resultant powder were determined. As a result, content of free $I_2$ was 0.2% by mass or less, and content of water was 5% by mass.

Example 3

As a wet body containing a DIH compound, 5,5-dimethyl-1,3-diiodohydantoin (21 g) containing water (8% by mass) was provided.

Water (22 g) as a solvent was further added to the wet body provided as described above to prepare a wet body in a slurry state.

The wet body in a slurry state as described above was charged into a lyophilizer, and cooled down to −80° C. to freeze the wet body. Subsequently, the resultant frozen body was dried by sublimation at 20° C. for 14 hours under reduced pressure condition of 270 Pa to obtain pale yellow crystalline powder of 5,5-dimethyl-1,3-diiodohydantoin in a purity of 98% or more.

After that, contents of free $I_2$ and water in the resultant powder were determined. As a result, content of free $I_2$ was 0.2% by mass or less, and content of water was 1% by mass.

<Storage Stability>

The pale yellow crystalline powders of 5,5-dimethyl-1,3-diiodohydantoin obtained in Examples 1 to 3 described above were stored each in hermetically sealed state in a polyethylene-made container at 5° C. As a result, no change in appearance of the compound or content of released $I_2$ was observed even after 6 months of time course.

Comparative Example 1

As a wet body containing a DIH compound, 5,5-dimethyl-1,3-diiodohydantoin (200 kg) containing n-butyl acetate (2% by mass) and water (13% by mass) was provided.

The wet body provided as described above was charged into a 1,000 L conical dryer, then, dried at 40 to 70° C. under a reduced pressure of 2,700 to 5,300 Pa.

As a result, decomposition of 5,5-dimethyl-1,3-diiodohydantoin started to proceed after about 4 hours from the start of drying, and $I_2$ was released. And after about 8 hours from the start of drying, vacuum line was blocked up by the released $I_2$. From then on, drying by the conical dryer could not be continued. In this case, the resultant 5,5-dimethyl-1,3-diiodohydantoin was red crystal, and contained 2% by mass or more of released $I_2$ and 8% by mass of water, and could not be used practically. In addition, this red crystal was stored in a hermetically sealed state in a polyethylene-made container at 5° C. Release of $I_2$ further proceeded within several weeks, and such appearance that released $I_2$ deposited in the upper part of the container was observed.

<Storage Test>

As a DIH compound, 5,5-dimethyl-1,3-diiodohydantoin (20 kg) (content of free $I_2$: 0.2% by mass, content of water: 1% by mass) was provided.

On the other hand, as storage containers, two bags made of polyvinylidene chloride/polyethylene composite material were provided.

In each storage container provided as described above, the DIH compound (10 kg each) also provided as described above was packed, then each bag was heat-sealed after the packing.

After that, one of the storage containers packed with the DIH compound was stored at 5° C. (Example), and the other was stored at 25° C. (Comparative Example). As a result, in the case of Example, no change in quality (specifically, content of released $I_2$) of the DIH compound was observed even after one year or more of storage. On the contrary, in the case of Comparative Example, decomposition of the DIH compound started to release $I_2$ after 2 months of storage, and coloration of the bag was observed.

From the results described above, it is indicated that decomposition of DIH compound and release of $I_2$ thereby in drying can be inhibited and a high quality of DIH compound which is easy to handle and superior in storage stability can be produced by subjecting wet body containing a DIH compound to fluidized drying or lyophilization. In addition, according to the storage method of the present invention, it is indicated that the DIH compounds are kept in high quality over long term.

Thus, according to the present invention, release of $I_2$ in production or storage of DIH compound can be inhibited, and thereby prevention of decrease in purity of the DIH compound or occurrence of various problems caused by $I_2$ can be expected.

It should be noted that, the present invention is based on JP Application No. 2005-25557 filed on 2 Sep., 2005, and the content of disclosure has been incorporated herein in its entirety by reference.

What is claimed is:

1. A production method for 1,3-diiodohydantoin compound, comprising:
    a step to prepare a composition comprising a 1,3-diiodohydantoin compound, and
    a step to dry the composition by contacting the composition with a heated gas to inhibit release of $I_2$ from the 1,3-diiodohydantoin compound so that a content of released $I_2$ of the 1,3-diiodohydantoin compound is 1% by mass or less and a content of water of the 1,3-diiodohydantoin compound is 6% by mass or less,
    wherein the composition is contacted by flowing with the heated gas, and
    wherein a flow rate of the heated gas in contact with the composition is 0.1 to 10.0 m/sec.

2. The production method according to claim 1, wherein the 1,3-diiodohydantoin compound is 5,5-dimethyl-1,3-diiodohydantoin.

3. The production method according to claim 1, wherein a temperature of the heated gas is 20 to 200° C.

4. The production method according to claim 1, wherein the step to dry the composition is performed under ordinary pressure.

* * * * *